US006592844B2

(12) United States Patent
Coombes et al.

(10) Patent No.: US 6,592,844 B2
(45) Date of Patent: Jul. 15, 2003

(54) PREPARATION OF PROTEIN MICROSPHERES, FILMS AND COATINGS

(75) Inventors: Allan G. A. Coombes, Nottingham (GB); Wu Lin, Nottingham (GB); Derek T. O'Hagen, Berkeley, CA (US); Stanley S. Davis, Nottingham (GB)

(73) Assignees: Chiron Corporation, Emeryville, CA (US); University of Nottingham, Nottingham (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/473,211

(22) Filed: Dec. 27, 1999

(65) Prior Publication Data
US 2002/0182146 A1 Dec. 5, 2002

Related U.S. Application Data

(63) Continuation of application No. 08/817,025, filed as application No. PCT/GB95/02393 on Oct. 10, 1995, now Pat. No. 6,007,791.

(30) Foreign Application Priority Data

Oct. 10, 1994 (GB) .............................. 9420355

(51) Int. Cl.⁷ .............. A61K 9/50; A61K 51/12; B01J 13/08; B01J 13/12
(52) U.S. Cl. .......... 424/1.29; 264/4.1; 264/4.6; 424/278.1; 424/491; 424/492; 424/493; 427/213.35; 427/430.1; 514/962
(58) Field of Search .............. 264/4.1, 4.6; 427/213.35, 427/430.1; 106/156.3; 424/1.29, 278.1, 491, 492, 493; 514/962

(56) References Cited

U.S. PATENT DOCUMENTS

| 1,366,380 A | 1/1921 | Grinnell .............. 427/430.1 X |
| 3,456,051 A | 7/1969 | Mima et al. ................. 424/455 |
| 4,400,376 A | 8/1983 | Sanderson ........... 424/278.1 X |
| 4,412,947 A | 11/1983 | Cicoa |
| 4,569,844 A | 2/1986 | Jones ...................... 264/4.3 X |
| 5,648,095 A | 7/1997 | Illum et al. .............. 264/4.6 X |
| 5,648,096 A | 7/1997 | Gander et al. .......... 424/492 X |
| 6,007,791 A * | 12/1999 | Coombes et al. .......... 424/1.29 |

FOREIGN PATENT DOCUMENTS

WO WO 91/06286 5/1991

* cited by examiner

Primary Examiner—Richard D. Lovering
(74) Attorney, Agent, or Firm—Roberta L. Robins; Alisa A. Harbin; Robert P. Blackburn

(57) ABSTRACT

A process is described for preparing microspheres, films and coatings from protein or modified protein in which the protein product is stabilized by carrying out the preparation in the presence of an aqueous solution of at least one α-hydroxy acid. The microspheres, films and coatings so produced have improved stability in aqueous solution.

38 Claims, No Drawings

PREPARATION OF PROTEIN MICROSPHERES, FILMS AND COATINGS

This application is a continuation of 08/817,025 filed Jul. 9, 1997 and now U.S. Pat. No. 6,007,791, which is a 371 of PCT/GB 95/02393 filed Oct. 10, 1995 which claims priority based on United Kingdom Application 9420355.1 filed Oct. 10, 1994.

The invention relates to microspheres, films and coatings made from proteins or modified proteins and in particular to improvements in the methods of preparation thereof which result in more stable products. The microspheres, films and coatings produced in accordance with the invention are suitable for a variety of biomedical applications.

The term "microspheres" is generally employed to describe colloidal particles which are substantially spherical and have a diameter in the range 10 nm to 2 mm. Particles having a diameter of less than 1 $\mu$ are sometimes called "nanoparticles". Microspheres made from a very wide range of natural and synthetic polymers have found use in a variety of biomedical applications. They can be labelled with markers (labels or sensing devices) and transported through various media both in-vitro and in-vivo. The labels may be chemical fluorescent, magnetic or radioactive and thus they may, by appropriate sensing equipment, be observed when in use. The sort of applications for which microspheres have been used are diagnostic screening, cell separation, immunoassays, studies of phagocytosis and blood flow, studies of cell motility, haemoperfusion and extracorporeal therapy, drug delivery devices, targeted drug delivery, cell encapsulation and endovascular embolisation.

An important property which microspheres must possess for biomedical applications is biocompatibility. They should be as resistant as possible to attack from the immune system in-vivo. Further, for many applications it is important that the microspheres be biodegradable and/or resorbable in the body once their function has been discharged. Also, in other cases, they should be small enough for easy introduction into the body.

For these reasons, naturally occurring polymer materials such as proteins have been the subject of much study for the preparation of microspheres. Nanoparticles as small as 100 nm can be prepared from, for example, albumin using certain preparation techniques and this is very useful for, among other things, injectable preparations.

Because of their biocompatability some proteins have been used in making coatings for artificial prostheses which will be introduced into the human body and therefore in contact with body fluids. As with microspheres any such coating should be as resistant as possible to attack from the immune system and furthermore should not be thrombolytic i.e. should cause only minimal platelet activation.

It is known that the blood biocompatibility of arterial prostheses is improved by coating the surfaces with albumin as demonstrated by Kottke-Marchant et al in Biomaterials 1989 10 147–155. Indeed albumin has been a particular material of choice for both coatings and microspheres because it is non-antigenic, biodegradable and readily available.

A number of methods are known for preparing protein microspheres and films and protein coatings for prostheses but certain drawbacks are associated with them all.

For example, a well-known method of preparing protein microspheres is suspension cross-linking. In this process an aqueous solution of protein is added to an immiscible liquid or oil phase. Droplets of protein are dispersed by high speed stirring and then hardening or stabilization of the droplets to form microspheres is brought about by heating of the suspension to, for example, a temperature above 80° C. or alternatively by chemical cross-linking employing a cross-linking agent such as glutaraldehyde. Various methods of preparation of albumin microspheres by the suspension cross-linking technique are described by Arshady in Journal of Controlled Release, 14 (1990) 111–131.

A disadvantage of preparing microspheres by the suspension cross-linking technique is that it is difficult to produce microspheres less than 500 nm in size, although nanospheres of about 100 nm diameter have been prepared using high power ultra-sonication. A further disadvantage is that the cross-linking agents used are often toxic which is not conducive to biocompatability.

Apart from suspension cross-linking protein microspheres, especially gelatin microspheres, have been prepared by coacervation or controlled desolvation. This procedure has also been used to prepare albumin microspheres in the size range 0.1 to 5 $\mu$m by Knop, et al (1975) using ethanol as the coacervation agent added to an aqueous solution of albumin. Ishizak et al (1985) have prepared albumin microspheres in the size range 0.5 to 1.5 $\mu$m using isopropyl alcohol as the coacervation agent. A similar technique has been developed to prepare 200–500 nm nanoparticles by adding acetone to an aqueous solution of human serum albumin and heating the colloidal system (Chen et al, 1994, J. Microencapsulation, 11, 395–407). In an alternative approach, chemical crosslinking agents such as glutaraldehyde have been used to harden the microspheres (Lin et al (1993) J. Drug Targeting 1 pp 237–243).

Coacervation methods for preparing protein microspheres are simpler to perform than suspension cross-linking methods and the particles are less toxic. A disadvantage however is that the particles are not particularly stable and aggregate easily to form larger microspheres. It has been difficult, to date, to use coacervation methods to prepare protein nanospheres around 200 nm or less which may have potential use as injectable preparations.

Albumin microparticles (2–10 $\mu$m) have also been prepared by spray drying followed by heat stabilisation at 100° C. or 150° C. for 6–24 hours (Pavanetto et al., J. Microencapsulation, 11, 445–454). The main advantage of spray drying is that albumin microparticles are free of oil residues or organic solvent and the process is useful for continuous operation.

The problems of toxicity of cross-linking agents and of stability also arise in the case of protein coatings to be applied to artificial prostheses. In particular, in the physiological environment the coating is subject to wear leaving areas of the prosthesis material exposed which may lead to an unwanted immune response or clot formation.

There is thus a continuing need for improved methods of preparation of protein microspheres, films and coatings which do not have the various disadvantages out-lined above. The present inventors have developed new methods of preparing protein microspheres, films and coatings which meet this goal and all the methods are based on the simple observation that when the pH of an aqueous albumin solution is lowered to about 4.4 to 4.7 with an $\alpha$-hydroxy acid, e.g. lactic acid, a rapid and extensive precipitate of albumen forms and this precipitate is unusually stable. The same effect is observed with other proteins although the pH range at which precipitation occurs varies.

Thus in its first aspect the invention provides a process for stabilizing a microsphere, film or coating made from at least one protein or modified protein which comprises preparing said protein microsphere, film or coating in the presence of an aqueous solution of at least one α-hydroxy acid or a derivative or analogue thereof.

It is to be understood that herein the term protein is intended to include peptides, polypeptides, metalloproteins, glycoproteins and lipoproteins and the term "modified protein" refers to proteins modified so as to have an additional molecule attached thereto, that would not naturally be associated with the protein. For example, the modified protein might consist of the protein conjugated to another organic polymer such as polyethylene glycol, polylactide or other polymer which can influence the surface characteristics of the microsphere, film or coating advantageously from a biocompatability point of view.

Preferred proteins which may be used in the process of the invention are albumen, gelatin, zein, casein, collagen or fibrinogen. Particularly preferred is albumen, either human serum albumen or ovalbumen.

Preferred α-hydroxy acids for use in the invention are glycolic acid, lactic acid, hydroxybutyric acid or mixtures of two or more thereof. Particularly preferred is lactic acid. By α-hydroxy acid derivative is meant an α-hydroxy acid derivatised by conjugation to another molecule, for example, polyethylene glycol, which may have a beneficial effect on the surface characteristics of the microspheres, films or coatings made by the process of the present invention.

Known processes as described above for making microspheres may be modified by combining with the stabilization method of the present invention to provide new and improved methods and products.

For example, a method of making a microsphere in accordance with one embodiment of the invention comprises the steps of:
 (a) mixing an aqueous solution of at least one protein or modified protein with an aqueous solution of at least one α-hydroxy acid or analogue or derivative thereof,
 (b) adding to the mixture prepared in step (a) a coacervation agent which results in the formation of mirospheres incorporating said protein or modified protein,
 (c) evaporating said coacervation agent and
 (d) recovering the microspheres from the aqueous solution.

As coacervation agent it is preferable to use acetone, ethanol or isopropanol and most preferably acetone. Its addition results in controlled desolvation of the microspheres which may then be recovered from the aqueous solution by centrifugation, sonication or filtration.

In the coacervation method described above a suitable protein concentration is about 0.1 to 10% by weight and the volume ratio of coacervation agent to protein solution is preferably about 2–3:1.

A particular advantage of the coacervation method described above is that the microspheres produced are nanoparticles e.g. about 200 nm. They are therefore suitable for making injectable preparations. It is possible to include in the nanoparticles during their preparation a pharmaceutically active agent for example or a material detectable by a bio-imaging procedure so that they may be detected in-vivo. This is achieved by including the active agent or bio-imaging material in the aqueous mixture of protein and α-hydroxy acid before the coacervation agent is added. Microspheres so produced can then be mixed with a pharmaceutically acceptable carrier or diluent to form a pharmaceutical composition or preparation suitable for bio-imaging. As aforesaid albumin, especially human serum albumin is particularly preferred for the preparation of microspheres for biomedical applications and lactic acid is the preferred stabilizer.

A method of making a microsphere in accordance with another embodiment of the invention comprises the steps of:
 (a) mixing an aqueous solution of at least one protein or modified protein with an aqueous solution of at least one α-hydroxy acid or analogue or derivative thereof,
 (b) adding the mixture prepared in step (a) to a water-immiscible oil,
 (c) stirring the mixture prepared in step (b) to form microspheres, and
 (d) recovering the micropheres from the water-immiscible oil.

Formation of microspheres in step (c) is enhanced if the stirring is carried out at an elevated temperature, for example at about 37 to about 50° C. Preferably, prior to the recovery step (d), a solvent is added to the microspheres prepared in step (c) to aid dispersion.

Microspheres produced by the above described emulsification method are usually in the 10 to 50 μm size range. The method allows the microspheres to be hardened without the addition of a toxic cross-linking agent which is a particular advantage. The protein solution is preferably more concentrated than with the coacervation method, about 10 to 30% by weight being particularly suitable. Preferably, the volume ratio of oil to aqueous phase is about 100.1. As the solvent for aiding microsphere dispersion, acetone or ethyl acetate can be used. A particularly preferred water-immiscible oil is soya oil. Albumin is the preferred protein with lactic acid as the stabilizer.

As with the coacervation method it is possible to add a pharmaceutically active agent or bio-imaging material to the aqueous phase before mixing with the oil and so produce microspheres suitable for use in pharmaceutical compositions or bio-imaging preparations.

Other known uses of microspheres in general include drug targeting and in-vivo diagnosis where it is desired to transport an active agent or detectable agent respectively to a particular site in the body. Microspheres made by both the coacervation and emulsification methods of the invention can be used in this way by attaching to the surface of a suitably loaded microsphere a molecule recognised by and having a particular affinity for a cellular receptor in the human or animal body. It is also possible to incorporate an antigenic material into the microspheres so that they can be mixed with a suitable pharmaceutical carrier and used as a vaccine.

In yet another aspect the invention provides a method of making a film from a protein or modified protein which comprises the particular steps of:
 (a) cooling to approximately 4° C. an aqueous solution of said protein or modified protein,
 (b) mixing the cooled solution prepared in step (a) with an aqueous solution of said α-hydroxy acid or an analogue or derivative thereof,
 (c) spreading the solution prepared in step (b) as a thin layer over a solid surface and
 (d) drying said thin layer to form a film.

Preferably the drying stage is carried out at between 50 and 70° C.

Albumin films made by the method of the invention have been shown to be much more resistant to dissolution in water than films made in the absence of the α-hydroxy acid.

Finally, in yet another aspect the invention provides a process for coating an article with a protein or modified protein layer which comprises dipping said article or a portion thereof into an aqueous solution comprising said protein or modified protein and an α-hydroxy acid.

In the alternative a previously protein-coated article may simply be dipped into the α-hydroxy acid solution.

In particularly preferred embodiments of all the methods described herein the protein and/or the α-hydroxy acid is modified or derivatised by attachment of another polymer which is known to influence the surface characteristics of the microsphere, film or coating produced. For example polyethylene glycol is known to have a beneficial effect on the surface of microspheres by rendering them more hydrophilic and thus resistant to sequestration by cells of the reticuloendothelial system. Thus the methods of the invention may be carried out using an α-hydroxy acid or protein conjugated to polyethylene glycol or other suitable polymer, for example polylactide.

The invention will now be described with reference to the following non-limiting Examples:

EXAMPLE 1

Preparation of Albumin Nanoparticles by the Coacervation Method

An aqueous albumin solution (ovalbumin or human serum albumin) was prepared at a concentration of 2% by weight and 2 mls of albumin solution were mixed with 20 μl lactic acid (LA) (F.W. 90.8; 85+% solution in water). 5.2 mls of acetone were then added and the mixture stirred overnight with a magnetic stirrer to evaporate the acetone. Nanoparticles were recovered from the aqueous solution by centrifuging and sonication and then resuspended in distilled water.

The size and Zeta potential of microspheres prepared as described above were measured and are shown in Table 1 below.

| Nanoparticles | Particle size (nm) | Zeta potential (mV) |
|---|---|---|
| LA stabilised HSA | 200 | −11.9 ± 0.9 |
| Glutaraldehyde stabilised HSA | 140 | −19.1 ± 0.7 |

A marked reduction in Zeta potential of lactic acid stabilized nanoparticles relative to glutaraldehyde stabilised nanoparticles was evident indicating differences in surface chemistry. The glutaraldehyde stabilised nanoparticles were prepared as described in Lin et al referred to above.

The nanoparticles stablised with lactic acid as described above have a particle size of 200 nm which renders them suitable for pharmaceutical use, particularly for injectable preparations. They are expected to be less toxic than albumin nanoparticles produced using glutaraldehyde crosslinking.

Nanoparticle suspensions appear to be stable over 7 days in water at room temperature. Ovalbumin precipitates are formed when the pH of ovalbumin solutions at 37° C. is adjusted to between 4.4 and 4.7 with lactic acid. These precipitates resist breakdown by 2% SDS solution when exposed for 72 hours at room temperature. A large component of the precipitate appears to be resistant to similar treatment in 5% SDS.

EXAMPLE 2

Preparation of Albumin Microspheres by the Emulsification Method 100 ml of soya oil containing 2% of Span 85 as a surfactant was stirred in an ice bath at 2000 rpm using an overhead stirrer. 1.0 ml of a 20% (w/v) aqueous solution of ovalbumin (OVA) was mixed with 100 μl of lactic acid and added dropwise to the soya oil which was stirred continuously. The resulting emulsion was stirred for 10 minutes and then for a further 30 minutes at 45° C. 50 ml of acetone or ethyl acetate (as a dispersion aid) was added and the suspension of hardened OVA microspheres was sonicated for 10 minutes. The OVA microspheres were separated by centrifuging and washed with acetone or ethyl acetate to remove residual oil.

Measurement of the microsphere size by laser light scattering revealed the diameter to be in the 10 to 50 μm range with the mean size around 25 μm.

Simple dissolution studies carried out in distilled water under ambient conditions revealed that the OVA microparticles prepared using lactic acid appeared to be physically stable for at least 3–5 days. In contrast, OVA microparticles produced using the above technique without lactic acid dissolved in less than 10 minutes.

EXAMPLE 3

Preparation of Ovalbumin Film

50 μl of lactic acid were added to 12 ml of a 2% solution of ovalbumin which had been cooled in an ice bath. 4 ml of the mixture were added to each of three 50 ml beakers and retained at 60° C. and 32° C. overnight and at room temperature for 16 hours respectively to obtain dried OVA films.

Films of ovalbumin were also produced by the above method but without addition of lactic acid.

A dissolution experiment was performed by adding 20 ml of distilled water to each beaker and measuring the concentration of free albumin in solution over time at room temperature. This was achieved by measuring the absorbance of the dissolution medium at 280 nm using a UV spectrophotometer and comparing this with a calibration curve constructed from a series dilution of ovalbumin in water. The percentage film dissolution is shown in Table 2 as a function of time.

TABLE 2

OVA film dissolution vs time at room temperature.

| Time | | % Film dissolution | | | | | | |
|---|---|---|---|---|---|---|---|---|
| (hours) | | 0.25 | 1 | 4 | 6 | 24 | 48 | 96 |
| OVA | RT* | 92.5 | 94.4 | | | | | |
| OVA/LA | | 42.5 | 100.0 | | | | | |
| OVA | 32 | 87.5 | 100.0 | | | | | |
| OVA/LA | | 47.5 | 100.0 | | | | | |
| OVA | 60 | 77.5 | 94.4 | | | | | |
| OVA/LA | | 25.0 | 38.9 | 36.1 | 38.9 | 38.9 | 41.7 | 41.7 |

*Film drying temperature

The data presented in Table 2 reveal that greater film stability is apparent when lactic acid is added to OVA solutions before drying. A marked improvement is obtained when OVA films containing lactic acid are dried at 60° C.

The film forming technique described above is particularly useful for coating medical textiles such as those used for arterial grafts and soft tissue repair so as to decrease permeability and improve biocompatibility.

What is claimed is:

1. A process for stabilizing a protein microsphere made from at least one protein, wherein said at least one protein comprises albumen, gelatin, collagen, zein, casein and/or fibrinogen, which comprises preparing said protein microsphere in the presence of an aqueous solution of at least one α-hydroxy acid or derivative thereof, wherein the derivative is selected from the group consisting of a polyethylene glycol conjugate and a polylactide conjugate.

2. A process as claimed in claim 1 wherein said derivative of an α-hydroxy acid is an α-hydroxy acid conjugated to polyethylene glycol.

3. A process as claimed in claim 1 wherein said α-hydroxy acid is glycolic acid, lactic acid, α-hydroxybutyric acid or a mixture of two or more thereof.

4. A process as claimed in claim 3 wherein said α-hydroxy acid is lactic acid.

5. A process as claimed in claim 1 wherein said protein is human serum albumin.

6. A process as claimed in claim 1 wherein said protein is ovalbumin.

7. A process as claimed in claim 1 wherein said protein is modified by having another organic polymer attached thereto.

8. A process as claimed in claim 1 which comprises the steps of:
   (a) mixing an aqueous solution of said at least one protein with an aqueous solution of at least one α-hydroxy acid or derivative thereof, wherein the derivative is selected from the group consisting of a polyethylene glycol conjugate and a polylactide conjugate,
   (b) adding to the mixture prepared in step (a) a coacervation agent which results in the formation of microspheres incorporating said protein,
   (c) evaporating said coacervation agent, and
   (d) recovering the microspheres from the aqueous solution.

9. A process as claimed in claim 8 wherein said coacervation agent is selected from the group consisting of acetone, ethanol and isopropanol.

10. A microsphere prepared by the process of claim 8.

11. A process as claimed in claim 8 wherein prior to addition of the coacervation agent a pharmaceutically active agent is added to the mixture prepared in step (a).

12. A pharmaceutical composition which comprises a plurality of microspheres prepared by the process of claim 11 and a pharmaceutically acceptable carrier or diluent.

13. A process as claimed in claim 8 wherein prior to addition of the coacervation agent a material detectable by a bio-imaging procedure is added to the mixture prepared in step (a).

14. A bio-imaging preparation which comprises a plurality of microspheres prepared by the process of claim 13 and a pharmaceutically acceptable carrier or diluent.

15. A process as claimed in claim 8 which comprises the additional step of attaching to the surface of the microspheres so formed a molecule recognised by and having an affinity for a cellular receptor in the human or animal body.

16. A microsphere prepared by the process of claim 15.

17. A process as claimed in claim 8 which comprises the additional step of attaching to the surface of the microspheres so formed an antigenic material.

18. A vaccine which comprises a plurality of microspheres prepared by the process of claim 17 and a pharmaceutically acceptable carrier or diluent.

19. A microsphere prepared by the process of claim 17.

20. A process as claimed in claim 1 comprising the steps of:
   (a) mixing an aqueous solution of said at least one protein with an aqueous solution of at least one α-hydroxy acid or derivative thereof, wherein the derivative is selected from the group consisting of a polyethylene glycol conjugate and a polylactide conjugate,
   (b) adding the mixture prepared in step (a) to a water-immiscible oil,
   (c) stirring the mixture prepared in step (b) to form microspheres, and
   (d) recovering the microspheres from the water-immiscible oil.

21. A process as claimed in claim 20 which comprises the additional step of attaching to the surface of the microspheres so formed a molecule recognised by and having an affinity for a cellular receptor in the human or animal body.

22. A process as claimed in claim 20 which comprises the additional step of attaching to the surface of the microspheres so formed an antigenic material.

23. A microsphere prepared by the process of claim 20.

24. A process as claimed in claim 20 wherein prior to recovery from the water-immiscible oil a solvent is added to the microspheres prepared in step (c) to aid dispersion.

25. A process as claimed in claim 24 wherein the solvent added to aid dispersion is acetone or ethyl acetate.

26. A process as claimed in claim 25 wherein the microspheres are sonicated prior to recovery from the water-immiscible oil.

27. A process as claimed in claim 20 wherein a pharmaceutically active agent is added to the mixture prepared in step (a) prior to mixing with the water-immiscible oil.

28. A process as claimed in claim 27 which comprises the additional step of attaching to the surface of the microspheres so formed a molecule recognised by and having an affinity for a cellular receptor in the human or animal body.

29. A process as claimed in claim 27 which comprises the additional step of attaching to the surface of the microspheres so formed an antigenic material.

30. A pharmaceutical composition which comprises a plurality of microspheres prepared by the process of claim 27 and a pharmaceutically acceptable carrier or diluent.

31. A process as claimed in claim 20 wherein a material detectable by a bio-imaging procedure is added to the mixture prepared in step (a) prior to mixing with the water immiscible oil.

32. A process as claimed in claim 31 which comprises the additional step of attaching to the surface of the microspheres so formed a molecule recognised by and having an affinity for a cellular receptor in the human or animal body.

33. A process as claimed in claim 31 which comprises the additional step of attaching to the surface of the microspheres so formed an antigenic material.

34. A microsphere prepared by the process of claim 31.

35. A bio-imaging preparation which comprises a plurality of microspheres prepared by the process of claim 31, and a pharmaceutically acceptable carrier or diluent.

36. A process for stabilizing a protein microsphere made from at least one protein, wherein said at least one protein comprises albumen, gelatin, collagen, zein, casein, and/or fibrinogen which comprises the steps of:
   (a) cooling to approximately 4° C. an aqueous solution of said protein,
   (b) mixing the cooled solution prepared in step (a) with an aqueous solution of said α-hydroxy acid or derivative thereof, wherein the derivative is selected from the group consisting of a polyethylene glycol conjugate and a polylactide conjugate,
   (c) spreading the solution prepared in step (b) as a thin layer over a solid surface, and (d) drying said thin layer to form a film.

37. A process as claimed in claim 36 wherein said layer of solution is dried at between 50 and 70° C.

38. A microsphere made by the process of claim 36.

* * * * *